US00PP16108P2

(12) United States Plant Patent
Smith

(10) Patent No.: US PP16,108 P2
(45) Date of Patent: Nov. 8, 2005

(54) ***CHRYSANTHEMUM* PLANT NAMED 'YOERIN'**

(50) Latin Name: *Chrysanthemum×morifolium*
Varietal Denomination: Yoerin

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 17 days.

(21) Appl. No.: 10/937,763

(22) Filed: Sep. 8, 2004

(51) Int. Cl.[7] ..... A01H 5/00

(52) U.S. Cl. ..... Plt./297

(58) Field of Search ..... Plt./297

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yoerin', characterized by its upright, outwardly spreading and rounded plant habit; freely branching habit; dense and full appearance; uniform and freely flowering habit; small daisy-type inflorescences with elongated oblong-shaped ray florets; light purple-colored ray florets and bright yellow-colored disc florets; natural season flowering in mid-October in the Northern Hemisphere; and good garden performance.

2 Drawing Sheets

Botanical classification/cultivar designation: *Chrysanthemum×morifolium* cultivar Yoerin.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yoerin'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret coloration and good garden performance.

The new *Chrysanthemum* originated from a cross-pollination made in October, 1999 in Salinas, Calif., of the *Chrysanthemum×morifolium* cultivar Alcala, disclosed in U.S. Plant Pat. No. 10,211, as the female, or seed, parent with the *Chrysanthemum×morifolium* cultivar Grace, disclosed in U.S. Plant Pat. No. 7,642, as the male, or pollen, parent. The new *Chrysanthemum* was discovered and selected by the Inventor as a single flowering plant within the progeny of the stated cross-pollination grown in a controlled environment in Alva, Fla. in November, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Yoerin has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoerin'. These characteristics in combination distinguish 'Yoerin' as a new and distinct cultivar of *Chrysanthemum:*

1. Upright, outwardly spreading and rounded plant habit.
2. Freely branching habit; dense and full plants.
3. Uniform and freely flowering habit.
4. Small daisy-type inflorescences with elongated oblong-shaped ray florets.
5. Light purple-colored ray florets and bright yellow-colored disc florets.
6. Natural season flowering in mid-October in the Northern Hemisphere.
7. Good garden performance.

In side-by-side comparisons conducted in Alva, Fla. under natural season conditions, plants of the new *Chrysanthemum* differed from plants of the female parent, the cultivar Alcala, in the following characteristics:

1. Plants of the new *Chrysanthemum* flowered about five days earlier than plants of the cultivar Alcala.
2. Plants of the new *Chrysanthemum* and the cultivar Alcala differed in ray floret coloration as plants of the cultivar Alcala had darker-colored ray florets.

In side-by-side comparisons conducted in Alva, Fla. under natural season conditions, plants of the new *Chrysanthemum* differed from plants of the male parent, the cultivar Grace, in the following characteristics:

1. Plants of the new *Chrysanthemum* were slightly larger and more rounded than plants of the cultivar Grace.
2. Plants of the new *Chrysanthemum* had smaller inflorescences than plants of the cultivar Grace.
3. Plants of the new *Chrysanthemum* flowered more uniformly and about three weeks later than plants of the cultivar Grace.
4. Plants of the new *Chrysanthemum* and the cultivar Grace differed in ray floret coloration as plants of the cultivar Grace had orange-colored ray florets.

Plants of the new *Chrysanthemum* can be compared to plants of the *Chrysanthemum* cultivar Kimberly, disclosed in U.S. Plant Pat. No 9,026. In side-by-side comparisons conducted in Alva, Fla. under natural season conditions, plants of the new *Chrysanthemum* differed from plants of the cultivar Kimberly in the following characteristics:

1. Plants of the new *Chrysanthemum* were more compact and more rounded than plants of the cultivar Kimberly.
2. Inflorescences of plants of the new *Chrysanthemum* had smaller discs than inflorescences of plants of the cultivar Kimberly.
3. Plants of the new *Chrysanthemum* flowered about five days later than plants of the cultivar Kimberly.

Plants of the new *Chrysanthemum* can also be compared to plants of the *Chrysanthemum* cultivar Dinka, disclosed in U.S. Plant Pat. No. 12,915. In side-by-side comparisons conducted in Alva, Fla. under natural season conditions, plants of the new *Chrysanthemum* differed from plants of the cultivar Dinka in the following characteristics:

1. Plants of the new *Chrysanthemum* were more compact than plants of the cultivar Dinka.
2. Plants of the new *Chrysanthemum* had larger inflorescences than plants of the cultivar Dinka.
3. Ray florets of plants of the new *Chrysanthemum* were lighter in color than ray florets of plants of the cultivar Dinka.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yoerin' grown in a container.

The photograph on the second sheet comprises a close-up view of typical inflorescences of the cultivar 'Yoerin'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yoerin.

Commercial classification: Daisy-type garden *Chrysanthemum.*

Parentage:

*Female, or seed, parent.*—*Chrysanthemum×morifolium* cultivar Alcala, disclosed in U.S. Plant Pat. No. 10,211.

*Male, or pollen, parent.*—*Chrysanthemum×morifolium* cultivar Grace, disclosed in U.S. Plant Pat. No. 7,642.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown; rounded plant habit. Stems initially upright, then outwardly spreading. Freely branching with lateral branches potentially developing at every node. Vigorous.

*Plant height.*—About 17 cm.

*Plant diameter.*—About 40 cm.

*Lateral branches.*—Length: About 20 cm. Diameter: About 5 mm. Internode length: About 1 cm. Strength: Strong. Texture: Pubescent. Color: Close to 144A.

*Foliage description.*—Leaf arrangement: Alternate. Length: About 3.8 cm. Width: About 3.2 cm. Apex: Mucronate. Base: Attenuate. Margin: Palmately and deeply lobed; sinuses mostly divergent. Texture, upper and lower surfaces: Pubescent. Color: Developing and fully expanded foliage, upper surface: More green than 147A. Developing and fully expanded foliage, lower surface: Close to 147B. Venation, upper surface: Close to 146A. Venation, lower surface: Close to 147B. Petiole: Length: About 6 mm. Diameter: About 3 mm. Texture, upper and lower surfaces: Pubescent. Color, upper surface: Close to 147B. Color, lower surface: Close to 147C.

Inflorescence description:

*Appearance.*—Daisy-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences slightly cupped. Uniform and freely flowering; about 32 inflorescences develop per lateral branch. Inflorescences persistent. Inflorescences not fragrant.

*Flowering response.*—Under natural season conditions, plants flower in Mid-October in the Northern Hemisphere.

*Inflorescence bud (before showing color).*—Height: About 4 mm. Diameter: About 6 mm. Shape: Oblate. Color (lower surface of phyllaries): Close to 144A.

*Inflorescence size.*—Diameter: About 3.25 cm. Depth (height): About 1 cm. Disc diameter: About 1.1 cm. Receptacle diameter: About 4 mm. Receptacle height: About 4 mm.

*Ray florets.*—Shape: Elongated oblong. Length: About 1.6 cm. Corolla tube length: About 3 mm. Width: About 5 mm. Apex: Emarginate to acute. Margin: Fused. Texture: Smooth, glabrous; satiny. Surface: Concave to flat. Orientation: Initially upright, then somewhat upright. Number of ray florets per inflorescence: About 22 in about one to two whorls. Color: When opening and fully opened, upper surface: 155D overlain with close to 77A. When opening and fully opened, lower surface: 155D underlain with close to 77A.

*Disc florets.*—Shape: Tubular; apex dentate, five-pointed. Length: About 6 mm. Width, apex: About 2 mm. Width, base: About 1 mm. Number of disc florets per inflorescence: Numerous. Color: Immature: Close to 9A to 12A. Mature: Apex: Close to 12A. Mid-section: Close to 144B. Base: Close to 155D.

*Phyllaries.*—Quantity per inflorescence: About 22. Length: About 6 mm. Width: About 3.5 mm. Shape: Deltoid. Apex: Acute. Base: Truncate, fused. Margin: Entire. Texture, upper surface: Smooth, waxy. Texture, lower surface: Pubescent. Color, upper and lower surfaces: Close to 144A.

*Peduncle.*—Length: First peduncle: About 5.4 cm. Fourth peduncle: About 8.7 cm. Seventh peduncle: About 11.2 cm. Diameter: About 1 mm. Strength: Strong. Aspect: About 45 to 50° from vertical. Texture: Pubescent. Color: Close to 144A.

*Reproductive organs.*—Androecium: Present on disc florets only. Anther color: Close to 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Yoerin', as illustrated and described.

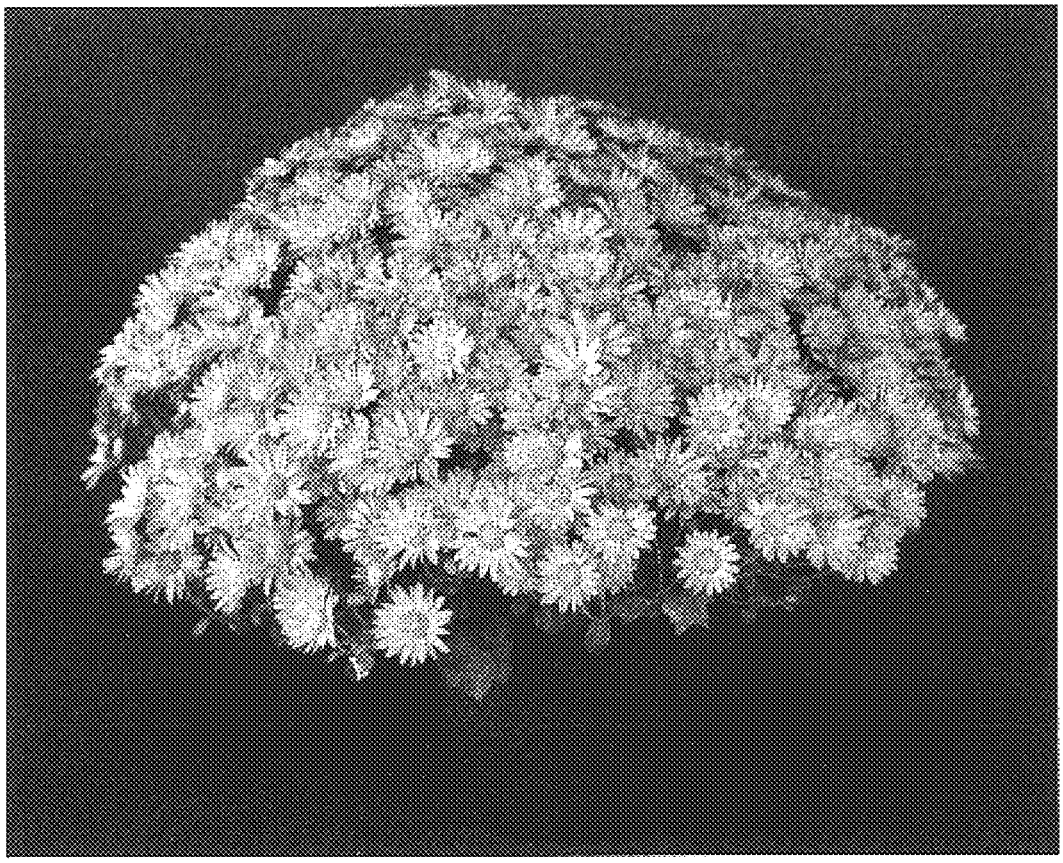

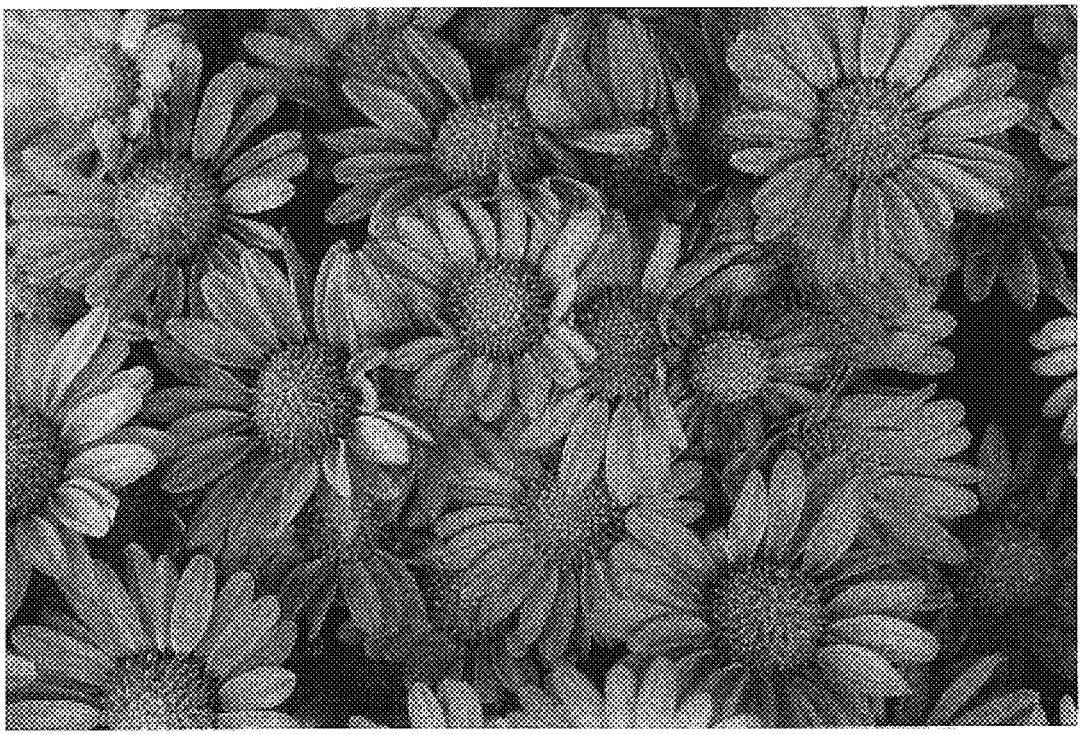

* * * * *